United States Patent [19]

Karl

[11] Patent Number: 4,540,510
[45] Date of Patent: Sep. 10, 1985

[54] SYNERGISTIC THICKENER MIXTURES OF AMPS POLYMERS WITH OTHER THICKENERS

[75] Inventor: Curtis L. Karl, New Hope, Minn.

[73] Assignee: Henkel Corporation, Minneapolis, Minn.

[21] Appl. No.: 579,242

[22] Filed: Feb. 13, 1984

[51] Int. Cl.$^3$ ............... C08B 37/00; C08F 128/02; C09K 7/00; G05D 24/00
[52] U.S. Cl. .................... 252/315.3; 8/552; 8/557; 8/558; 8/562; 166/308; 252/8.55 R; 252/153; 252/174.17; 252/174.21; 252/315.1; 252/545; 424/78; 424/81; 523/130; 526/287; 514/781; 514/782
[58] Field of Search ............ 252/8.55 R, 526, 545, 252/153, 174.17, 174.21, 174.23, 315.1, 315.3; 166/308; 424/81, 78, 361, 362, 363; 8/557, 558, 561, 562, 552; 523/130, 131, 132; 524/364; 526/287

[56] References Cited

U.S. PATENT DOCUMENTS

| | | |
|---|---|---|
| 3,743,613 | 7/1973 | Coulter, Jr. et al. ............ 523/130 |
| 3,898,037 | 5/1975 | Lange et al. ............ 134/3 |
| 3,931,089 | 1/1976 | Karl ............ 524/547 |
| 4,011,909 | 3/1977 | Adams et al. ............ 166/293 |
| 4,053,323 | 10/1977 | Adams et al. ............ 106/100 |
| 4,055,502 | 10/1977 | Swanson ............ 166/307 |
| 4,065,422 | 12/1977 | Lundmark et al. ............ 524/391 |
| 4,103,742 | 8/1978 | Swanson ............ 166/282 |
| 4,107,057 | 8/1978 | Dill et al. ............ 524/534 |
| 4,128,631 | 12/1978 | Lundmark et al. ............ 424/70 |
| 4,136,739 | 1/1979 | Salathiel et al. ............ 166/300 |
| 4,172,055 | 10/1979 | DeMartino ............ 523/130 |
| 4,191,657 | 3/1980 | Swanson ............ 166/282 |
| 4,240,505 | 12/1980 | Swanson ............ 166/307 |
| 4,244,826 | 1/1981 | Swanson ............ 524/27 |
| 4,246,124 | 1/1981 | Swanson ............ 524/27 |
| 4,323,123 | 4/1982 | Swanson ............ 166/283 |
| 4,330,441 | 5/1982 | Böhmer et al. ............ 523/457 |
| 4,412,027 | 10/1983 | Klein et al. ............ 524/364 |
| 4,425,241 | 1/1984 | Swanson ............ 252/8.5 A |
| 4,440,228 | 4/1984 | Swanson ............ 252/8.55 D |
| 4,460,627 | 7/1984 | Weaver et al. ............ 427/221 |
| 4,461,884 | 7/1984 | Peiffer et al. ............ 526/287 |
| 4,476,033 | 10/1984 | Josephson ............ 166/307 |
| 4,490,308 | 12/1984 | Fong et al. ............ 526/287 |
| 4,499,232 | 2/1985 | Engelhardt et al. ............ 524/548 |

FOREIGN PATENT DOCUMENTS

| | | | |
|---|---|---|---|
| 2836289 | 3/1979 | Fed. Rep. of Germany | 526/287 |
| 1197323 | 7/1970 | United Kingdom | 526/287 |

*Primary Examiner*—Dennis L. Albrecht
*Attorney, Agent, or Firm*—Ernest G. Szoke; Patrick J. Span; J. Daniel Wood

[57] ABSTRACT

Synergistic thickener mixture comprising a mixture of a polymer of 2-acrylamido-2-methylpropane sulfonic acid and certain water soluble polymers such as the galactomannan gums, derivatives thereof, cellulose derivatives and polyoxyalkylene oxide polymers. The composition finds utility in earth formation fracturing, textile print pastes, suspending pigments in paints and gelling alcohol-based cosmetic formulations.

11 Claims, No Drawings

SYNERGISTIC THICKENER MIXTURES OF AMPS POLYMERS WITH OTHER THICKENERS

BACKGROUND OF THE INVENTION

This invention relates to thickener compositions which show synergistic thickening effects. The compositions are mixtures of a polymer of 2-acrylamido-2-methylpropane sulfonic acid and certain water soluble polymers such as the galactomannan gums, derivatives thereof, cellulose derivatives and polyalkylene oxide polymers.

Various polymers have been used in the past to thicken liquids such as water, alcohols and mixtures thereof. Problems sometimes occur such as insufficient viscosity levels, rapid viscosity degradation, insolubility or precipitation of the polymer hydrolysis products through insolubilization by multivalent ion salts. The homopolymers of 2-acrylamido-2-methylpropane sulfonic acid have more recently come of interest but thickened solutions possessing greater viscosities and/or suspending power are desired. Illustrative patents relating to the use of such polymers are U.S. Pat. Nos. 3,931,089, 4,065,422, 4,128,631, 4,332,688 and 4,242,098. The galactomannan gums such as guar and locust bean have been long recognized as producing high viscosity sols. Processes of producing such gums from their beans can be seen from U.S. Pat. Nos. 2,891,050, 3,455,899, 353,823 and 3,132,681. Derivatives of such gums such as hydroxyalkyl ethers have found particular utility in formation fracturing applications such as seen in U.S Pat. No. 3,483,121. Other known thickeners are the polyalkylene oxide polymers, such as those of polyethylene oxide, and the alkyl ethers of cellulose.

SUMMARY OF THE INVENTION

It has now been found that mixture of the polymers of 2-acrylamido-2-methylpropane sulfonic acid with these other known thickeners produce viscosities in aqueous or alcohol media which are in excess of the additive viscosities produced by the components used individually. These synergistic effects are observed in both aqueous and anhydrous alcohol solvent systems.

The mixtures of polymers of acrylamido-methylpropane sulfonic acid with the other thickeners such as the galactomannan gums or derivatives thereof, polyethylene oxide polymers and the cellulose alkyl ethers find utility in the areas where the polymers are used individually. Thus, the mixture with hydroxypropyl guar will find particular utility in earth formation fracturing for oil well stimulation because of this particular rheology. Examples of other applications include thickening textile print pastes and suspending pigments in paints as well as gelling alcohol-based cosmetic formulations.

DETAILED DESCRIPTION OF THE INVENTION

The acrylamido-methylpropane sulfonic acid polymers employed in the present invention are prepared from an acrylamido-methylpropane sulfonic acid, such as, 2-acrylamido-2-methylpropane sulfonic acid, which is commercially available and sold under the trademark "AMPS" by the Lubrizol Corporation.

It has the structural formula:

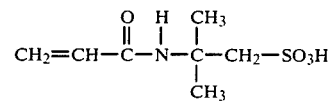

Polymerization of this monomer is known in the art and described by the Lubrizol Corporation as follows:

"The following recipes are given as a guide to the homopolymerization and copolymerization of AMPS (2-acrylamido-2-methylpropanesulfonic acid) monomer and its sodium salt. The polymerizations, except where noted otherwise, should be conducted in a resin flask equipped with a stirrer, gas inlet tube, condenser and thermometer. All solutions should be purged for one hour with nitrogen or argon before adding the initiator, with purging continued during the polymerization. All amounts are in grams.

| AMPS (2-acrylamido-2methylpropane sulfonic acid) Monomer | 100 |
|---|---|
| Distilled Water | 100 |
| Ferrous Sulfate Heptahydrate | 0.01 |
| Hydrogen Peroxide 0.05% Solution | 0.25 |

Prepare a solution of AMPS monomer in water in an 800 ml beaker. Purge. Add the ferrous sulfate and hydrogen peroxide. The solution gels almost instantly. The temperature rises to 75°–80° in about two minutes. Cool to room temperature. Cut gel into pieces and dry at 60° in a vacuum oven."

In addition, preparation of the polymers can be found in the U.S. patents noted in the background discussion above and may also be found described in Canadian Pat. No. 864,433, as well as other publications dealing with the preparation of these materials.

The polymers can also be further generally defined as those having the repeating linkage

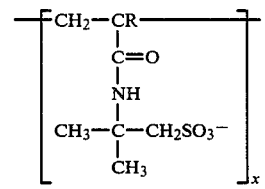

where x is value substantially defining the molecular weight of the product and R is H or $CH_3$. The terminal groups, which generally have, little bearing on the desired properties are most often hydrogen, but may also be others such as hydroxyl, sulfate, sulfonate, or

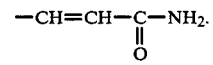

The cation, which may be designated as M, associated with the anionic portion will generally be H, for the acid form, and in the salt form will preferably be sodium, potassium, ammonium, monoethanolamine, diethanolamine triethanolamine and mixtures thereof. In the present invention the polymers preferably have a molecular weight above 5,000,000 but polymers having lower molecular weights down to about 1,000,000, may also be used. It is generally desirable to employ a polymer having a molecular weight of at least 3,000,000. However polymers at the lower end of the range of about 1,000,000 molecular are now being offered as of Feb. 18, 1983 by Henkel Corporation under the tradename "RHEOTHIK". A polymer having a molecular weight of about 4,000,000 would have a Brookfield viscosity, using a No. 1 spindle at 2.5 rpm on a solution in water of 0.5% by weight concentration of about 1370 cps. The polymers employed in the examples herein gave a viscosity of 3000–6000 cps under the same conditions indicating molecular weights in excess of 5,000,000 but generally below 10,000,000.

The polymerization reaction is generally described as temperature, pH, and catalyst sensitive. In addition it is desirable to exclude oxygen from the reaction vessel used to form the polymer as that material inhibits the polymerization process. The catalysts which are included to enhance the rate of polyerization are materials such as ammonium bisulfite, ferrous sulfate, hydrogen peroxide, sodium metabisulfite, or other redox catalysts. Catalysts are particularly useful when monomers of lower purity, or lower solids concentration, i.e. 30% solid by weight in water are employed. When monomers of high purity and high concentration, 50% by weight, are employed catalysts are generally not required to produce polymerization.

The homopolymers employed in the examples below illustrating the present invention were prepared from the higher (50%) concentration in water using a mixture of potassium persulfate, potassium metabisulfite, and ferrous sulfate catalyst. Nitrogen is bubbled through the mixture until polymerization begins. The polymerization begins in about 30 minutes and is accompanied by an increase in temperature. The reaction is completed within 30 minutes. The resulting gel after cooling is then cut up and dried overnight in a vacuum oven at aspirator pressure and a temperature of about 50° C. Then the polymer is ground to powder.

Polymers of the lower weights can be prepared following the procedures found in Example I and II, U.S. Pat. Nos. 4,065,422 and 4,128,631 referred to earlier above.

As indicated earlier, the other thickener polymers used in admixture with the acrylamido-methylpropane sulfonic acid polymers to provide a synergistic effect are the galactomannan gums, polyalkylene oxide polymers and cellulose alkyl ethers. The galactomannan gums includes the class of polysaccharides containing both galactose and mannose units. The polygalactomannans are usually found in the endosperm section of leguminous seeds such as guar, locust bean, honey locust and flametree. Derivatives of these gums such as the hydroxy alkyl ethers are particularly useful in admixture with the acrylamidomethylpropane sulfonic acid polymers.

As described in U.S. Pat. No. 3,483,121, the hydroxylakyl galactomannan gums are made by reacting galactomannan gums, such as guar gum and locust bean gum, with an alkylene oxide having at least two and preferably three or more carbon atoms. Galactomannan gums are composed of units of galactose and mannose sugars, each having an average of three reactive hydroxyl groups. These react with alkylene oxides to produce a hydroxyalkyl ether of the gum. Each unit of alkylene oxide added to the galactomannan gum in turn creates a new hydroxyl group, which is itself reactive. Theoretically there is no limit to the amount of alkylene oxide which may be added to the galactomannan gums. As a practical matter, however, a degree of molar substitution (M.S.) of about 4 to 5 imposes a practical upper limit. Thus, for purposes of the present invention the hydroxyalkyl galactomannan gums will generally involve a degree of molar substitution of from 0.1 to 5. These degrees of substitution are achieved by reacting the alkylene oxide with the gum, employing 0.1 to 6 oxirane equivalents from the alkylene oxide per anhydrohexose unit of the gum.

Briefly, the hydroxyalkyl ether product is prepared by reacting an alkylene oxide having at least 2 carbon atoms, with a galactomannan gum. Alkylene oxides having up to 8 carbon atoms may be employed. Generally, the oxirane group is a terminal vicinal epoxy group. The alkylene oxides may be represented by the following formula:

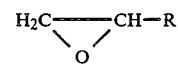

where R is hydrogen or an alkyl group having from 1 to 6 carbon atoms. R is preferably methyl, such as in propylene oxide. R may also, however, be ethyl, propyl, butyl, amyl or hexyl.

For convenience the preparation will be described with particular reference to guar gum which is an old and well-known commercially available material. Basically, the hydroxyalkyl ether guar gum product is prepared by the reaction of guar gum with the alkylene oxide in the presence of an alkaline catalyst. Commercially available guar gum generally contains from about 8 to 15% moisture by weight. For further convenience, the preparation of the product will hereinbelow be described with reference to the reaction of guar gum with propylene oxide to provide mono- or poly-hydroxypropyl-ether of guar gums. The rate of reaction is dependent on the catalyst concentration and the temperature. Temperatures substantially higher than room temperature will generally require pressure equipment or solvent reflux. The reaction may be illustrated in its simplest, idealized form by the following equation:

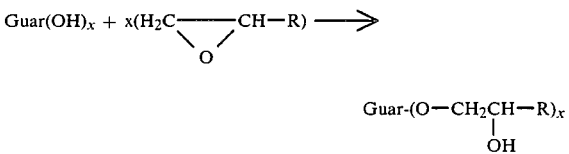

With propylene oxide the R group is methyl. With other alkylene oxides, having a terminal, vicinal epoxide group, the R group will be an alkyl group having 2 carbon atoms less than the alkylene group of the alkylene oxide. Preferably R will contain from 1 to 6 carbon atoms.

Because the alkylene oxide may also react with the hydroxyl group attached to the secondary carbon atom of the alkyl group, subsequent to the reaction of a molecule of alkylene oxide with one of the reactive hydroxyl groups of the guar gum, a complex product may be produced which may be illustrated by the idealized formula

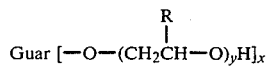

where x is an integer up to 3 and y is an integer dependent on the degree of molar substitution. It is difficult to specify the exact integers for x and y in any one specific product and accordingly, the product is described by reference to the degree of molar substitution (M.S) which indicates the amount of alkylene oxide reacted.

In view of the complex nature of the product, it is difficult to define the product by any simple chemical name. The products are most conveniently defined as a hydroxyalkyl ether of guar in which the alkyl group has at least 2 carbon atoms, preferably 3 to 8 carbon atoms, and the hydroxyl group is attached to a seondary carbon atom. In this manner, both the idealized simple ethers and the complex products are encompassed.

As indicated, the presence of an alkaline catalyst is necessary. Such catalysts are in general the alkali metal or alkaline earth metal hydroxides, such as sodium, potassium or calcium hydroxide. Very small amounts of catalyst may be employed, as low as 0.05% based on the weight of guar gum. However, the rate of reaction is increased with increasing amounts of catalyst and, accordingly, higher amounts of catalyst are generally employed. The exact amount will depend to some extent on the other process conditions. In general, however, about 2 to 3% is employed.

The reaction may be conducted at room temperature or elevated temperatures. At room temperature, the reaction is slower. Where temperatures other than room temperature are employed, temperatures on the order of about 50°–100° C. are generally used with temperatures in the range of 60° to 90° C., particularly the higher temperatures, being preferred.

As indicated, the reaction may be conducted at atmospheric pressure, under reflux, or at elevated pressures in a closed reactor. The exact pressure is not critical and while higher pressures may be employed, operation is normally conducted at whatever pressure develops during the reaction. Generally, such developed pressures will be on the order of from about 30 to 125 p.s.i.g. In most reactions where the temperature is below 100° C., the maximum pressures will be in the range of 60 to 80 p.s.i.g. The exact pressure will generally be dependent on the particular temperature employed.

The time of reaction is generally dependent on the temperature, amount of alkylene oxide employed and the degree of substitution desired. At room temperature long periods of time are required, particularly where high degrees of substitution are desired. At higher temperatures, under reflux or under pressure, shorter time periods of 5 hours or less are employed. Under the slowest conditions times up to 100 hours may be required.

The reaction may be conducted in the substantial absence of water or solvent (no water added), but because the efficiency of reaction is very low without the addition of water the reaction is generally conducted in the presence of water. In the absence of other solvents, catalytic amounts of water on the order of about 3 to 8% based on the gum, are employed, these small amounts generally being employed where higher temperatures and elevated pressures are employed. Where lower temperatures and atmospheric pressure is employed, generally larger amounts of water will be employed. Further, other organic solvents will be employed. Illustrative of such organic solvents are isopropanol (water-miscible) and heptane (water-immiscible). Other less preferred unreactive organic solvents may be employed including common aliphatic hydrocarbons having from 5 to 10 carbon atoms, such as heptane and hexane; alkanols higher than methanol, those having from 2 to 6 carbon atoms, such as t-butanol; the only requirement being that the solvent be substantially unreactive. Where higher water levels are employed, the water should be sufficient to swell the guar gum slightly, thereby making the gum more reactive. When employed with a solvent, such as isopropanol or heptane, from 10 to 80% water based on the weight of guar gum is employed; from 30 to 70% with the water-miscible solvents and 20 to 30% with the water-immiscible solvents.

Generally, the water-miscible solvents, an amount equal to the weight of gum up to three times the weight of gum is employed. With water-immiscible solvents, an amount of from 3 to 5 times the weight of gum is generally employed. With the organic solvents, the ratio by weight of water to organic solvent is preferably within the range of from 0.2 to 0.45 for the water-miscible organic solvents and from 0.1 to 0.2 for the water-immiscible organic solvents. In general, any unreactive, organic solvents may be employed.

As indicated earlier, other polymers which are employed in admixture with the acrylamido-methylpropane sulfonic acid polymers are the water soluble cellulose ethers and the polyalkylene oxide polymers. These polymers are well known and can be produced in accordance with known procedures. The cellulose ethers which may be used among others are the hydroxyl containing cellulose ethers such as hydroxyalkyl cellulose corresponding to the hydroxy alkyl ethers of galactomannans above such as hydroxyethyl and hydroxypropyl cellulose and the alkylhydroxyalkyl celluloses such as methylhydroxypropyl cellulose. The most common polyalkylene oxide polymers which are available commercially are the poly(ethylene oxide) polyether polymers.

The polymer mixture is then dissolved in the particular liquid to be thickened. The liquid system or compositions to which the polymer may be added to provide the desired results are those containing water or alcohol or mixtures thereof. Thus, the invention finds utility in aqueous systems and finds particular utility however in alcohol systems, either anhydrous or aqueous containing systems.

The mixture is used in amounts of .01 to 10% by weight based on the weight of liquid, i.e. water and/or alcohol, and more desirably from 0.1 to 5% with about 0.5% being the most preferred. The optimum amount will vary dependent on the particular liquid system, particular other polymer in admixture with the acrylamido-methyl propane sulfonic acid polymer and the ratio of the polymers in the mixture. The ratio of sulfonic acid polymer to other polymer in the mixture can vary between about 90:10 to 10:90 (or about 90–10% by weight), more desirably 80:20 to 20:80. The optimum ratio will depend on the particular liquid system, the concentration level of the mixture and the specific polymer employed in admixture with the sulfonic acid polymer. The maximum synergism for a mixture of guar and sulfonic acid polymer with a concentration level of 0.5% in water is provided at a guar to sulfonic acid ratio of 1:1 or 50:50. With a polyethylene oxide polymer (Polyox-coagulant grade) a maximum synergism at pH 7 occurs at a ratio of about 4:1 sulfonic acid polymer to polyethylene oxide polymer, at a 0.5% concentration level. In non-aqueous systems such as anhydrous methanol, at a 0.5% concentration level of a mixture of hydroxypropyl guar and sulfonic acid polymer a ratio of guar to sulfonic acid polymer of 90:10 provide maximum synergism.

The following examples will serve to further illustrate the invention in which all percentages and parts are by weight unless otherwise noted.

EXAMPLE I

The experimental procedure employed in collecting the data which follows was as follows. Weighed samples of each polymer were mixed together at selected ratios (moisture-free basis). The dry mixture was added quickly to the vortex of water in a Warning Blender running at low speed. The mixture was agitated for 2 minutes or less if the solution thickened sufficiently to support undissolved particles. The sols were transferred to glass beakers and allowed to hydrate. Brookfield or Fann Viscometers were used to measure viscosities after 2 and 24 hours of hydration, all viscosities being determined at room temperature, i.e. about 23° C.

Several different homopolymers of acrylamido-methyl propane sulfonic acid were employed in the examples which are summarized in the Tables to follow, in which the polymers designated as (A) are identified as PAM-followed by a sample number.

The other polymer employed in admixture with the acrylamido-methylpropane sulfonic acid polymer, designated (B) polymer in the Tables are identified in accord with the following code:

| Code | Polymer |
|---|---|
| PEO | Polyethylene oxide polymer - Polyox Coagulant Grade available from Union Carbide Corporation |
| G | Guar gum - GALACTOSOL ® 210 Polymer available from Henkel Corporation |
| LB | Locust Bean Gum - SUPERCOL ® 912 Polymer available from Henkel Corporation |
| T | Tara gum - SNG-200 available from Nutralgum S.p.A. (Italy) |
| HEG | Hydroxyethyl guar gum - HE 1 available from Celanese Polymer Specialties Company |
| HELB | Hydroxyethyl locust bean gum - experimental gum (M.S. = about 0.1) |
| HPLB-1 | Hydroxypropyl locust bean gums - experimental gum (M.S. = about 0.3) |
| HPLB-2 | Hydroxypropyl locust bean gums - experimental gum (M.S. = about 0.4) |
| HEC | Hydroxyethylcellulose - National 250H available from Hercules, Inc. |
| HPG | Hydroxypropyl guar - GENGEL ® E-9 Polymer (M.S. = 0.4) available from Henkel Corporation |
| HPG-X | Developmental hydroxypropyl guar XG-499S (M.S. = 1.2) |
| HPC | Hydroxypropyl cellulose - Klucel H available from Hercules, Inc. |

Tables 1 and 2 tabulate raw viscosity data for these polymers and mixtures thereof in water, and alcohols. Tables 3 and 4 summarize key data from the former tables to better illustrate the presence and relative degree of viscosity synergism in the polymer mixtures. Two methods were employed to define expected viscosities of the various two component mixtures. One method assumes a linear relationship between the component viscosities and therefore uses a weighted average of the viscosities of each component for predicting viscosities of mixtures. This method is an approximation because viscosity-concentration relationships are non-linear, but it serves as a simple estimator of the viscosity of the mixture which will generally over estimate the actual value, thereby providing a small buffer zone. The second method uses weighted averages of the logarithms of the pure component viscosities which is more accurate, but also more complicated.

TABLE 1

| | | WATER AS SOLVENT | | | | | | |
|---|---|---|---|---|---|---|---|---|
| | | 2.5 rpm Viscosities[5] | | | | | | |
| | (A) Polymer | Wt. Ratio (B)/(A) | | | | | | |
| (B) Polymer | Sample No. | 100/0 | 90/10 | 70/30 | 50/50 | 30/70 | 10/90 | 0/100 |
| PEO | PAM-779 | Not determined | | | | | | |
| G | PAM-832 | 912 | 2400 | 2816 | 3088 | 3520 | 3824 | 4192 |
| G | PAM-783 (Na) | 720 | 1584 | 2880 | 3320 | 3200 | 2800 | 2600 |
| LB | PAM-832 | 48 (512)[4] | 528 | 1488 | 2368 | 3104 | 3768 | 3888 |
| T | PAM-832 | 144 | 872 | | 2432 | | | 3917[3] |
| HEG | PAM-832 | 204 | 2208 | 3008 | 3296 | 3520 | 3760 | 3920 |
| HELB | PAM-784 | | | | | | | |
| HEC | PAM-832 | 192 | 640 | 936 | 2565 | 3264 | 3920 | 3917[3] |
| HPG | PAM-832 | 480 | 1392 | 3456 | 3520 | 3680 | 3760 | 3776 |
| HPG-X | PAM-832 | 128 | 1184 | 2064 | 2784 | 3184 | 3776 | 3808 |
| HPLB-1 | PAM-832 | 84 | 496 | 1564 | 3040 | 3648 | 3776 | 3776 |
| HPLB-2 | PAM-832 | 48 | 464 | 1688 | 2736 | 3344 | | 3917[3] |
| HPC | PAM-832 | 64 | 1088 | 2048 | 2144 | 3032 | 3992 | 3917 |

*80/20 Wt. Ratio
**20/80 Wt. Ratio
[3]Average value
[4]5/95 Wt. Ratio
[5]2 hour hydration time
[6]Moisture free basis

TABLE 1a

WATER AS SOLVENT

| (B) Polymer | (A) Polymer Sample No. | 20 rpm Viscosities[5] Wt. Ratio (B)/(A) | | | | | | |
|---|---|---|---|---|---|---|---|---|
| | | 100/0 | 90/10 | 70/30 | 50/50 | 30/70 | 10/90 | 0/100 |
| PEO | PAM-799 | 70 | *(600) | | 1000 | **(1160) | | 1420 |
| G | PAM-832 | 568 | 688 | 726 | 770 | 880 | 904 | 930 |
| G | PAM-783 (Na) | 476 | 704 | 1000 | 1020 | 960 | 770 | 760 |
| LB | PAM-832 | 38 | 204 | 490 | 648 | 778 | 910 | 927 |
| | | | (294) | | | | | |
| T | PAM-832 | 125 | 412 | | 724 | | | 930 |
| HEG | PAM-832 | 162 | 900 | 902 | 870 | 902 | 942 | 990 |
| HELB | PAM-784 | 54 | *(340) | | 612 | **(812) | | 930 |
| HEC | PAM-832 | 152 | 310 | 712 | 852 | 906 | 940 | 942 |
| HPG | PAM-832 | 312 | 588 | 982 | 930 | 920 | 936 | 942 |
| HPG-X | PAM-832 | 96 | 428 | 528 | 704 | 758 | 896 | 908 |
| HPLB-1 | PAM-832 | 82 | 230 | 488 | 1028 | 1048 | 994 | 918 |
| HPLB-2 | PAM-832 | 48 | 264 | 642 | 834 | 904 | | 936[3] |
| HPC | PAM-832 | 50 | 386 | 493 | 568 | 681 | 944 | 936[3] |

*80/20 Wt. Ratio
**20/80 Wt. Ratio
[3] Average value
[4] 5/95 Wt. Ratio
[5] 2 hour hydration time
[6] Moisture free basis

TABLE 2

ALCOHOLS AS SOLVENTS

| Alcohol | (B) Polymer | (A) Polymer Sample No. | | 20 rpm Brookfield Viscosities Wt. Ratio (B)/(A) | | | | | | |
|---|---|---|---|---|---|---|---|---|---|---|
| | | | | 100/0 | 90/10 | 70/30 | 50/50 | 30/70 | 10/90 | 0/100 |
| MeOH | HPG-X | PAM-801 | (2 hr) | 15 | 203 | 220 | 250 | 296 | 374 | 450 |
| | | | (24 hr) | 15 | 667 | 520 | 600 | 420 | 440 | 452 |
| MeOH* | HPC | PAM-832 | (2 hr) | 96 | 168 | 296 | 304 | 278 | 234 | 198 |
| EtOH* | HPC | PAM-832 | (2 hr) | 26 | 78 | 120 | 130 | — | — | 102 |
| | | | (24 hr) | 40 | 126 | 180 | 180 | — | — | 116 |
| 95% EtOH* | HPC | PAM-832 | (2 hr) | 75 | 178 | 248 | 254 | — | — | 193 |
| i-PrOH* | HPC | PAM-832 | (2 hr) | 266 | 444 | 406 | 284 | 224 | 160 | 114 |

*hot alcohol (60–70° C.)

TABLE 2a

ALCOHOLS AS SOLVENTS

| Alcohol | (B) Polymer | (A) Polymer Sample No. | | 1000 rpm Fann Viscosities Wt. Ratio (B)/(A) | | | | | | |
|---|---|---|---|---|---|---|---|---|---|---|
| | | | | 100/0 | 90/10 | 70/30 | 50/50 | 30/70 | 10/90 | 0/100 |
| MeOH | HPG-X | PAM-801 | (2 hr) | 22 | 25 | 32 | 32 | 35 | 38 | 43 |
| | | | (24 hr) | 22 | 130 | 45 | 45 | 42 | 39 | 44 |
| MeOH* | HPC | PAM-832 | (2 hr) | | | | | | | |
| EtOH* | HPC | PAM-832 | (2 hr) | 45 | 61 | 73 | 74 | — | — | 61 |
| | | | (24 hr) | 55 | 84 | 98 | 94 | — | — | 66 |
| 95% EtOH* | HPC | PAM-832 | (2 hr) | 74 | 102 | 157 | 180 | — | — | 91 |
| i-PrOH* | HPC | PAM-832 | (2 hr) | 66 | 72 | 66 | 51 | 45 | 37 | 33 |

*hot alcohol (60–70° C.)

TABLE 3

WATER AS SOLVENT

| (Polymer) | Viscosity 20 rpm | (A) Polymer | Viscosity 20 rpm | B/A Wt. Ratio | Estimated** Viscosity (cP) | Calculated** Viscosity (cP) | Actual** Viscosity (cP) |
|---|---|---|---|---|---|---|---|
| PEO | 70 | PAM-779 | 1420 | 80/20 | 340 | 130 | 600 |
| G | 568 | PAM-832 | 930 | 90/10 | 600 | 600 | 690 |
| G | 476 | PAM-783 (Na) | 760 | 70/30 | 560 | 550 | 1000 |
| LB | 38 | PAM-832 | 927 | 70/30 | 300 | 100 | 490 |
| T | 125 | PAM-832 | 930 | 90/10 | 200 | 150 | 410 |
| HEG | 162 | PAM-832 | 990 | 90/10 | 240 | 190 | 900 |
| HELB | 54 | PAM-784 | 930 | 80/20 | 220 | 100 | 340 |
| HEC | 152 | PAM-832 | 942 | 70/30 | 380 | 260 | 710 |
| HPG | 312 | PAM-832 | 942 | 70/30 | 500 | 430 | 980 |
| HPG | 96 | PAM-832 | 908 | 90/10 | 170 | 120 | 430 |
| HPLB-1 | 82 | PAM-832 | 918 | 50/50 | 500 | 270 | 1030 |
| HPLB-2 | 48 | PAM-832 | 936* | 70/30 | 300 | 120 | 640 |

TABLE 3-continued

| | | | WATER AS SOLVENT | | | | |
|---|---|---|---|---|---|---|---|
| (Polymer) | Viscosity 20 rpm | (A) Polymer | Viscosity 20 rpm | B/A Wt. Ratio | Estimated** Viscosity (cP) | Calculated** Viscosity (cP) | Actual** Viscosity (cP) |
| HPC | 50 | PAM-832 | 936* | 90/10 | 140 | 70 | 390 |

*Average value
**Rounded to nearest tenth

TABLE 4

| | | | ALCOHOLS AS SOLVENTS | | | | | |
|---|---|---|---|---|---|---|---|---|
| Alcohol | (B) Polymer | Viscosity 20 rpm (cP) | (A) Polymer | | Viscosity 20 rpm (cP) | B/A Wt. Ratio | Estimated** Viscosity (cP) | Calculated** Viscosity (cP) | Actual** Viscosity (cP) |
| MeOH | HPG-X | 15 | PAM-801 | (2 hr) | 450 | 90/10 | 60 | 20 | 200 |
| | | 15 | | (24 hr) | 452 | 90/10 | 60 | 20 | 670 |
| MeOH* | HPC | 96 | PAM-832 | (2 hr) | 198 | 70/30 | 130 | 100 | 300 |
| EtOH* | HPC | 26 | PAM-832 | (2 hr) | 102 | 50/50 | 60 | 50 | 130 |
| | | 40 | | (24 hr) | 116 | 50/50 | 80 | 70 | 180 |
| 95% EtOH* | HPC | 75 | PAM-832 | (2 hr) | 193 | 50/50 | 130 | 120 | 250 |
| i-PrOH* | HPC | 226 | PAM-832 | (2 hr) | 114 | 90/10 | 250 | 240 | 440 |

*Hot alcohol (60–70° C.)
**Rounded to nearest tenth

The embodiments of the invention in which an exclusive property or privilege is claimed are defined as follows:

1. A composition comprising a mixture of a polymer of an acrylamido methylpropanesulfonic acid having a molecular weight of above about one million and a water soluble polymer selected from the group consisting of galactomannan gums, hydroxyalkyl ethers of galactomannan gums, hydroxyalkyl cellulose ethers, polyalkylene oxide polymers and mixtures thereof, wherein the alkyl and alkylene groups contain from 2 to 8 carbon atoms, said polymers in said mixture being in a ratio to synergistically thicken liquids.

2. A compositions as defined in claim 1 wherein said acrylamido polymer contains the repeating linkage.

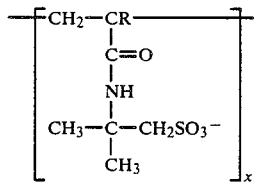

wherein x has a value such that the molecular weight is at least 1,000,000 and R is H or CH₃.

3. A composition as defined in claim 1 wherein said acrylamido polymer is a homopolymer of 2-acrylamido-2-methyl propane sulfonic acid.

4. A composition as defined in claim 3 wherein said homopolymer is the sodium salt.

5. A composition as defined in claim 1 wherein said acrylamido polymer comprises from 10 to 90% by weight of the mixture.

6. A composition as defined in claim 1 wherein said water soluble polymer is selected from the group consisting of guar gum, locust bean gum, tara gum, hydroxyethyl guar, hydroxypropyl guar, hydroxyethyl locust bean, hydroxypropyl locust bean, hydroxyethyl cellulose, hydroxypropyl cellulose and polyethylene oxide.

7. A thickened liquid composition comprising a liquid selected from the group consisting of water, an alcohol and mixtures thereof and a thickener, said thickener comprising a mixture of a polymer of an acrylamido methylpropanesulfonic acid and a water soluble polymer selected from the group consisting of galactomannan gums, hydroxyalkyl ethers of galactomannan gums, hydroxyalkyl cellulose ethers, polyalkylene oxide polymers and mixtures thereof, wherein the alkyl and alkylene groups contain from 2 to 8 carbon atoms, said polymers in said mixture being in a ratio to synergistically thicken said liquids.

8. A thickened composition as defined in claim 7 wherein said acrylamido polymer contains the repeating linkage.

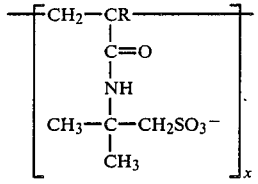

wherein x has a value such that the molecular weight is at least 1,000,000 and R is H or CH₃.

9. A thickened composition as defined in claim 7 wherein said acrylamido polymer is a homopolymer of 2-acrylamido-2-methyl propane sulfonic acid.

10. A thickened composition as defined in claim 7 wherein said water soluble polymer is selected from the group consisting of guar gum, locust bean gum, tara gum, hydroxyethyl guar, hydroxypropyl guar, hydroxyethyl locust bean, hydroxypropyl locust bean, hydroxyethyl cellulose, hydroxypropyl cellulose and polyethylene oxide.

11. A thickened composition as defined in claim 7 wherein said thickener is employed in an amount of 0.01 to 10% by weight based on said liquid and the ratio of acrylamido polymer to water soluble polymer is in the range of 90:10 to 10:90 by weight.

* * * * *